United States Patent [19]

Distler et al.

[11] 4,323,783

[45] Apr. 6, 1982

[54] TOMOGRAPHIC APPARATUS FOR PRODUCING TRANSVERSE LAYER IMAGES

[75] Inventors: Walter Distler; Erich Kintopp, both of Erlangen, Fed. Rep. of Germany

[73] Assignee: Siemens Aktiengesellschaft, Berlin & Munich, Fed. Rep. of Germany

[21] Appl. No.: 141,058

[22] Filed: Apr. 17, 1980

[30] Foreign Application Priority Data

May 29, 1979 [DE] Fed. Rep. of Germany ....... 2921820

[51] Int. Cl.³ ............................................. A61B 6/00
[52] U.S. Cl. ................................ 250/445 T; 250/513
[58] Field of Search .................... 250/445 T, 511, 513

[56] References Cited

U.S. PATENT DOCUMENTS 4,227,088  10/1980  Mayden et al. ................. 250/445 T Primary Examiner—Alfred E. Smith
Assistant Examiner—T. N. Grigsby Attorney, Agent, or Firm—Hill, Van Santen, Steadman, Chiara & Simpson

[57] ABSTRACT

In an exemplary embodiment, a radiation measuring arrangement contains a radiation source as well as a radiation receiver which determines the radiation intensity behind the radiography subject. For irradiation of the radiography subject from different directions a rotating device for the measuring arrangement is present. A measured value converter calculates a layer image from the signals supplied by the radiation receiver. Between the radiation source and the radiation receiver, two hollow cylinders consisting of radiation-absorbing material having equal diameters and a common axis are arranged between which a gap for the passage of the x-ray beam is left open and into which the radiography subject can be inserted. The two hollow cylinders are adjustably mounted for relative displacement in an axial direction for the purpose of adjustment of the gap width.

3 Claims, 3 Drawing Figures

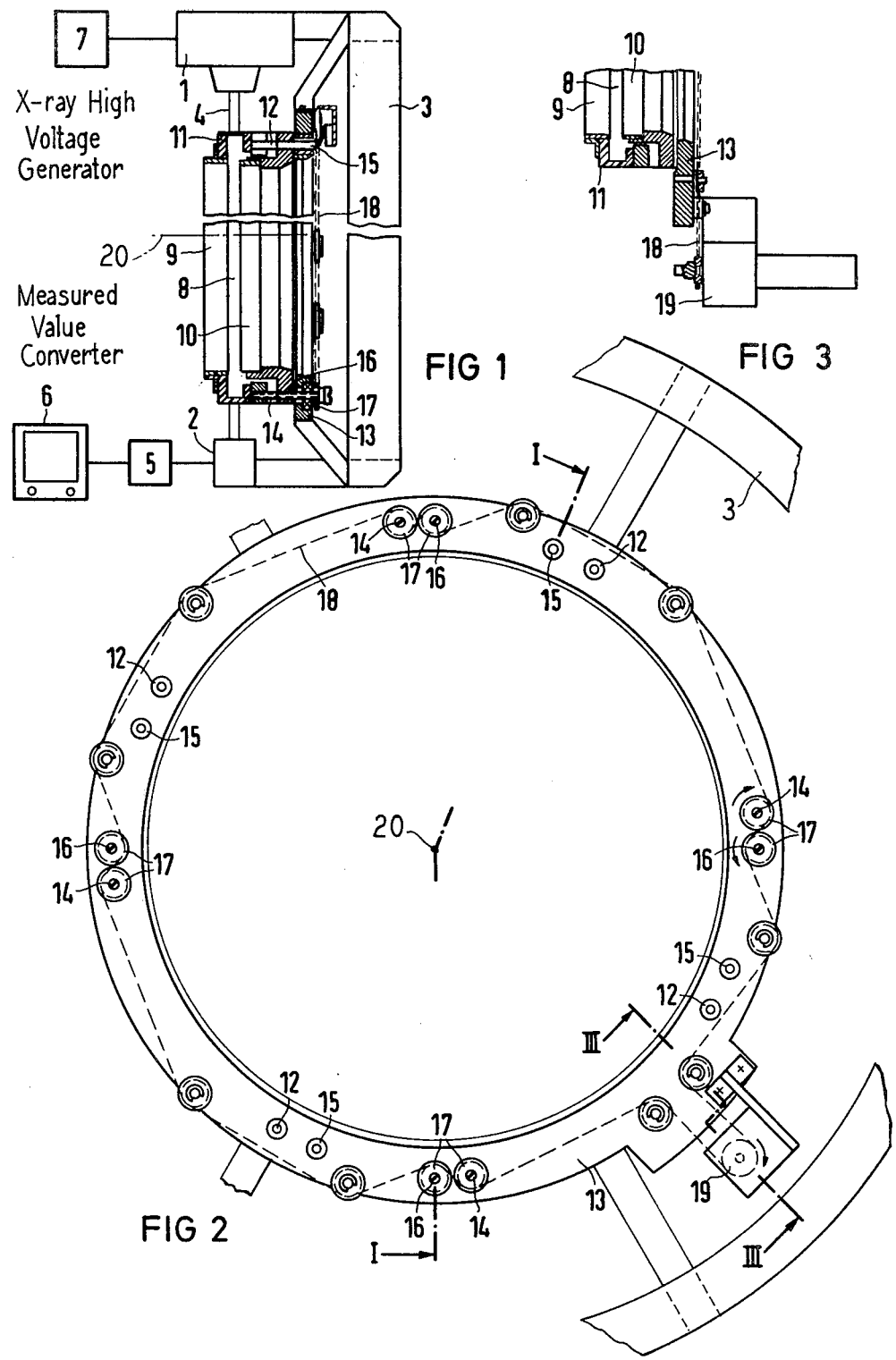

TOMOGRAPHIC APPARATUS FOR PRODUCING TRANSVERSE LAYER IMAGES

BACKGROUND OF THE INVENTION

The invention relates to a tomographic apparatus for producing transverse layer images of a radiography subject comprising a radiation measuring arrangement which contains a radiation source which produces a beam of rays, penetrating the radiography subject, the cross sectional extent of the beam perpendicular to the layer plane being equal to the layer thickness, as well as containing a radiation receiver which determines the radiation intensity behind the subject, comprising a rotating device for the measuring arrangement for the purpose of penetrating the radiography subject by radiation from various directions, and comprising a measured value converter for the transformation of the signals supplied by the radiation receiver into a layer image in which, between the radiation source and the radiation receiver, two hollow cylinders of radiation-absorbing material are disposed having the same diameters and a common axis between which a gap for the passage of the x-ray beam is left open, the radiography subject being supported so that the layer to be examined is within the confines of the cylinders and aligned with the plane of the gap.

A tomographic apparatus of this type is described in the patent application No. P 28 50 675.4. The two hollow cylinders here effect a suppression of the stray radiation in the instance in which the radiation receiver is designed as a stationary detector ring as well as in the case in which the radiation receiver is rotated together with the radiation source for scanning of the radiography subject.

SUMMARY OF THE INVENTION

The object underlying the invention resides in designing a tomographic apparatus of the type initially cited such that the thickness of the examined layer is adjustable.

This object is achieved in accordance with the invention in that the two hollow cylinders, for the adjustment of the gap width, are adjustably mounted for relative displacement in an axial direction. The gap width here determines the thickness of the examined layer.

An expedient embodiment of the invention, in which no ray-absorbing parts interfere with the x-ray beam, provides that the hollow cylinders are adjustably guided on a supporting ring, and that the hollow cylinder remote from the supporting ring is connected with its guide means mounted on the supporting ring via an intermediate ring permeable to x-rays, which ring covers the gap. The x-radiation can thus penetrate the intermediate ring in an unobstructed fashion.

The invention shall be explained in greater detail in the following on the basis of an exemplary embodiment illustrated on the accompanying drawing sheet; and other objects, features and advantages will be apparent from this detailed disclosure and from the appended claims.

BRIEF DESCRIPTION OF THE DRAWINGS

FIG. 1 shows a fragmentary section of a tomographic apparatus according to the invention;

FIG. 2 shows a lateral view of the supporting ring for the hollow cylinders in the case of the tomographic apparatus according to FIG. 1, FIG. 2 showing the sectional line I—I on which FIG. 1 is taken; and FIG. 3 shows a partial section according to the line III—III in FIG. 2.

DETAILED DESCRIPTION

In FIG. 1 an x-ray tube 1 and a radiation receiver 2 are illustrated which are mounted on a rotating ring 3. The x-ray tube 1 emits a fan-shaped beam of rays whose lateral extent lies in a plane disposed perpendicularly to the drawing plane. The transmitted beam is received by the detectors of the radiation receiver 2. The number of detectors of the radiation receiver 2, which are disposed in a series, and the aperture angle of the beam of rays 4 (the angle included between the laterally outermost diverging rays of the fan-shaped beam) are so matched to one another that a cross section of a radiography subject, arranged between the x-ray tube 1 and the radiation receiver 2, is traversed (or permeated) by x-radiation. The radiography subject is scanned during a scanning operation in which a rotating ring 3 with the x-ray tube 1 and the radiation receiver 2 is rotated through an angle of 360°. The output signals of the radiation receiver 2 which are thus generated are received by a measured value converter 5, containing a computer, which calculates therefrom the image of the examined cross section of the radiography subject and effects its reproduction on a video unit or monitor 6. The x-ray tube 1 is supplied by an x-ray high voltage generator 7.

The thickness of the examined cross section of the radiography subject is determined by the width of a gap 8 which is left open between two hollow cylinders 9, 10, consisting of radiation-absorbing material; for example, lead. The hollow cylinder 9 is connected, via an intermediate ring; namely, a plastic ring 11, which is transmissive to x-radiation and covers the gap 8, with column guides 12 which are guided in a supporting ring 13. The supporting ring 13 is mounted on the rotating ring 3. In addition, the plastic ring 11 is connected with threaded spindles 14 which are likewise guided in the supporting ring 13.

Like the hollow cylinder 9, the hollow cylinder 10 is also mounted on the supporting ring 13. It is guided on the supporting ring 13 by column guides 15, on the one hand, and by threaded spindles 16, on the other hand.

As is particularly apparent from FIG. 2, there are seated on the threaded spindles 14 and 16 pinions 17 via which a length of chain 18 is guided. The chain 18 is additionally guided via deflection pulleys guided on the supporting ring 13, not illustrated in greater detail in FIG. 2, and is driven by a drive motor 19 visible in FIGS. 2 and 3. The threads of the threaded spindles 14 and 16 are selected such that, during drive of the chain 18 in the one direction, the hollow cylinders 9, 10, are moved axially toward one another, and, during drive in the other direction, are moved axially away from one another. Thus, via the drive 19, the gap width between the hollow cylinders 9 and 10 and hence the scanned layer thickness is adjustable. The cylinders 9, 10 suppress, in every position, the stray radiation issuing from the radiography subject inserted in the interior of the hollow cylinders 9 and 10. The radiography subject, if necessary, can thus be pushed through the supporting ring 13 and the rotating ring 3.

From FIG. 1 it is apparent that the two hollow cylinders 9 and 10 possess the same diameter and a common axis 20. The hollow cylinder 9 remote from the carrier ring 13 is connected with its guide means 12, 14, mounted on the carrier ring 13 via the plastic ring 11.

It will be apparent that many modifications and variations may be effected without departing from the scope of the novel concepts and teachings of the present invention.

I claim as my invention:

1. Tomographic apparatus for producing transverse layer images of a radiography subject, comprising a radiation measuring arrangement which contains a radiation source which produces a beam of rays penetrating the radiography subject, the cross sectional extent of the beam perpendicular to the layer plane being equal to the layer thickness, as well as containing a radiation receiver which determines the radiation intensity behind the subject, a rotating device for the measuring arrangement for irradiating the radiography subject from different directions and a measured value converter for the transformation of the signal supplied by the radiation receiver into a layer image, and beam confining means between the radiation source and the radiation receiver comprising two hollow cylinders of radiation-absorbing material having the same diameters and a common axis, between which a radiation permeable gap for the passage of the x-ray beam is left open and into which the radiography subject can be inserted, characterized in that the two hollow cylinders (9, 10), for the adjustment of the gap width, are adjustably mounted for relative displacement in an axial direction.

2. Tomographic apparatus according to claim 1, characterized in that the hollow cylinders (9, 10) are adjustably guided on a supporting ring (13).

3. Tomographic apparatus according to claim 2, with said rotating device comprising a supporting ring (13) axially adjacent said hollow cylinders (9, 10), the hollow cylinder (9) remote from the supporting ring (13) having an intermediate ring (11) transmissive of x-rays, and guide means (12, 14) mounted on the supporting ring (13) and mounting said intermediate ring (11) transmissive to x-rays for displacement with said hollow cylinder remote from the supporting ring, said intermediate ring (11) covering said gap in all positions of relative adjustment of said hollow cylinders.

* * * * *